United States Patent [19]

Desai

[11] Patent Number: 5,215,103
[45] Date of Patent: Jun. 1, 1993

[54] CATHETER FOR MAPPING AND ABLATION AND METHOD THEREFOR

[76] Inventor: Jawahar M. Desai, 2721 West Browning, Fresno, Calif. 93711

[21] Appl. No.: 406,917

[22] Filed: Sep. 13, 1989

Related U.S. Application Data

[60] Division of Ser. No. 68,833, Jun. 10, 1987, Pat. No. 4,940,064, which is a continuation-in-part of Ser. No. 931,696, Nov. 14, 1986, abandoned.

[51] Int. Cl.⁵ .............................................. A61N 1/04
[52] U.S. Cl. ..................... 128/784; 128/786; 604/105
[58] Field of Search ............... 128/639, 642, 656, 657, 128/658, 772, 774, 419 D, 419.5, 783, 784, 786, 303.14, 303.15, 303.11, 303.12, 362, 395, 397, 398; 604/20, 105; 606/27-29, 32, 41, 45, 46, 47

[56] References Cited

U.S. PATENT DOCUMENTS

| | | |
|---|---|---|
| 4,112,952 | 9/1978 | Thomas et al. ............... 128/419 P |
| 4,154,247 | 5/1979 | O'Neill ........................ 128/419 P |
| 4,365,639 | 12/1982 | Goldreyer. | |
| 4,386,615 | 6/1983 | Sowton ........................... 128/786 |
| 4,660,571 | 4/1987 | Hess et al. ....................... 128/784 |

FOREIGN PATENT DOCUMENTS 2310775 12/1976 France .......................... 128/786

Primary Examiner—William E. Kamm
Assistant Examiner—John P. Lacyk
Attorney, Agent, or Firm—Majestic, Parsons, Siebert & Hsue

[57] ABSTRACT

A multipolar electrode catheter includes a central and four side electrodes at its distal end. The catheter is actuable from a retracted or collapsed mode wherein the side electrodes are arranged around the tubular catheter outer surface to an expanded mode. A plurality of longitudinal slits in the catheter wall enable radial expansion of the distal end so that the side electrodes are moved to an operative position radially outward from their position in the retracted mode. In the expanded position, the side electrodes lie in the same plane and equally spaced from adjacent electrodes. Electrode leads connected to the electrodes enable the electrodes to be used both for mapping and ablation of endocardial sites.

21 Claims, 4 Drawing Sheets

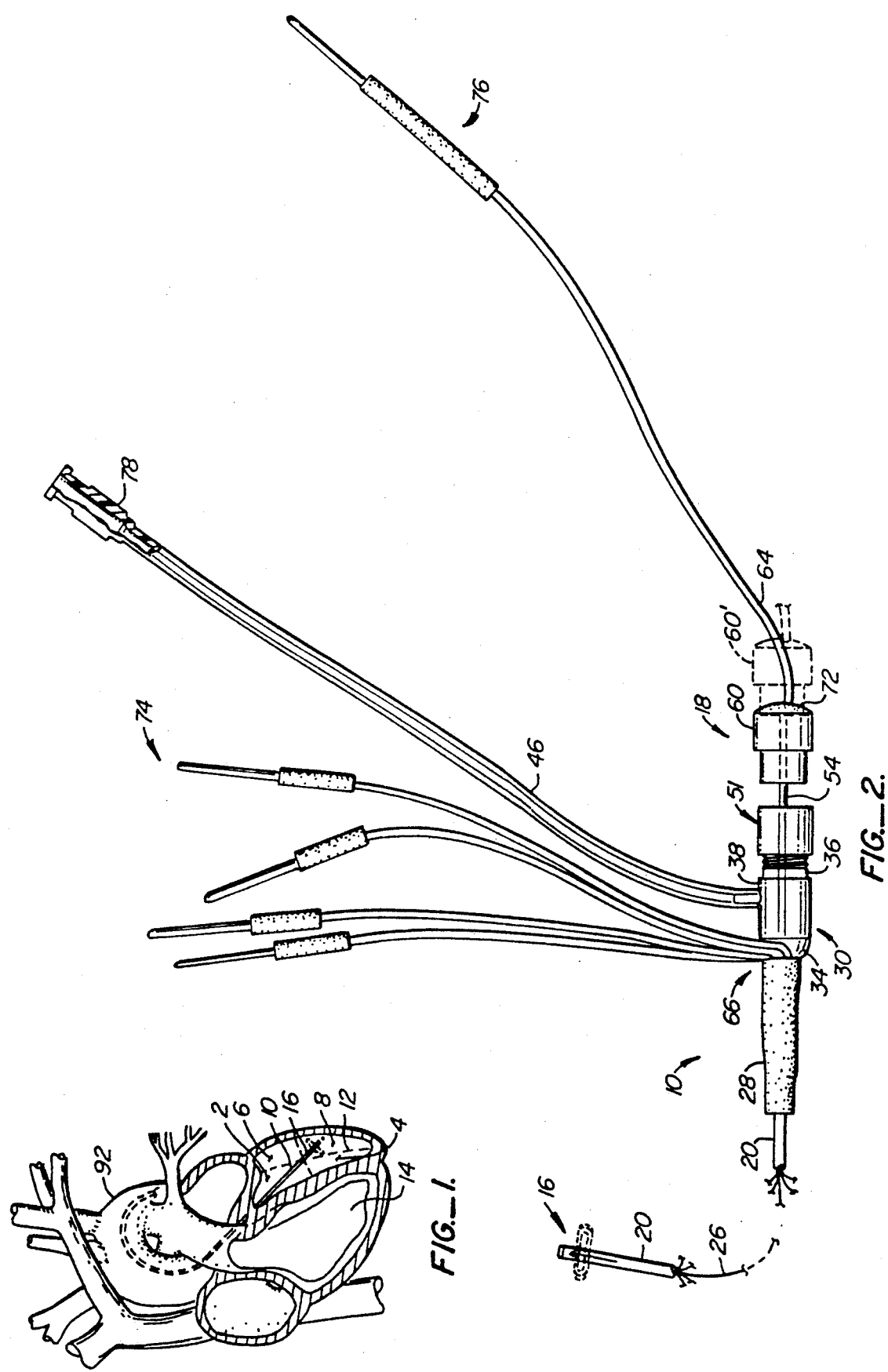

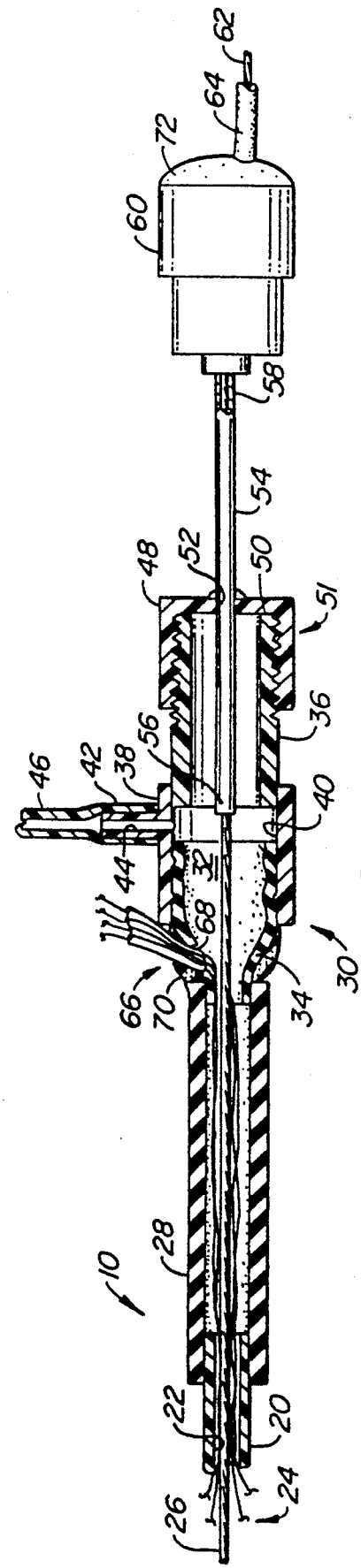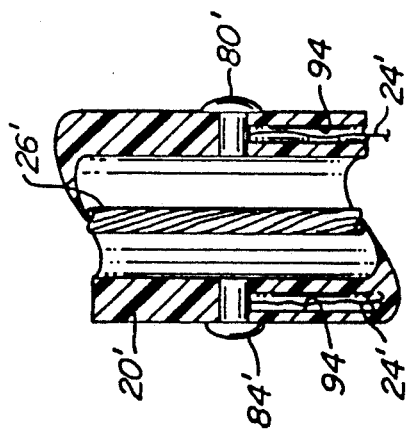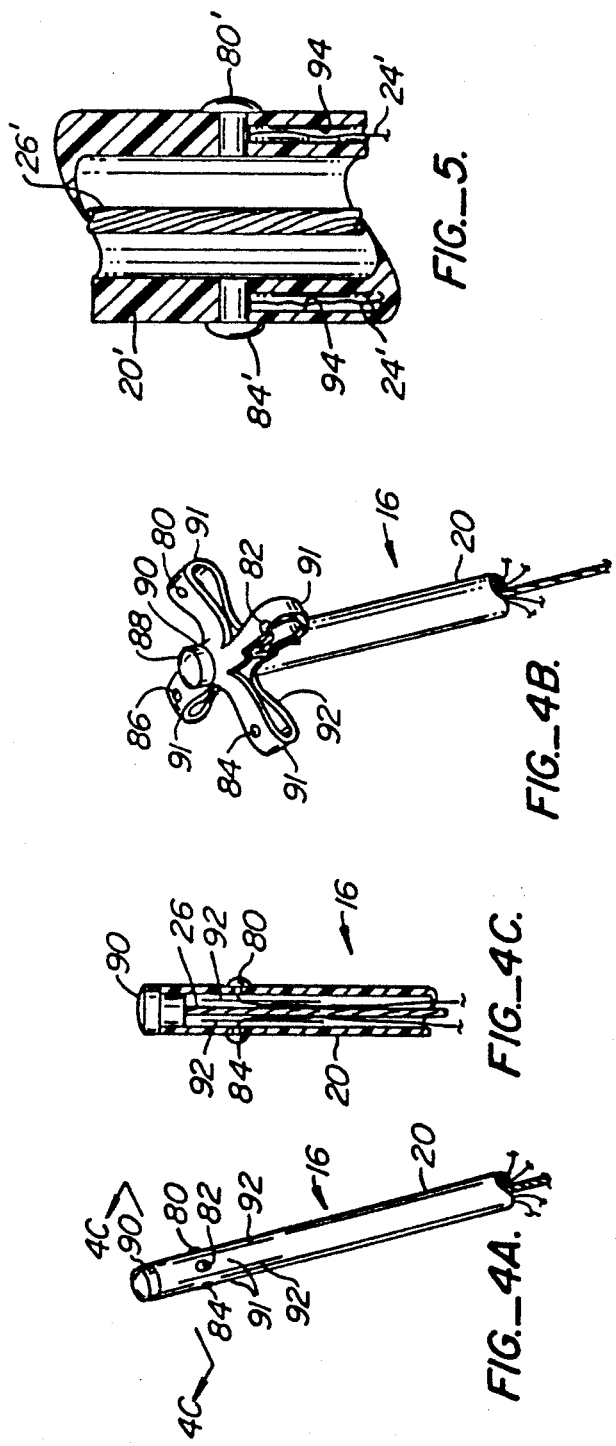

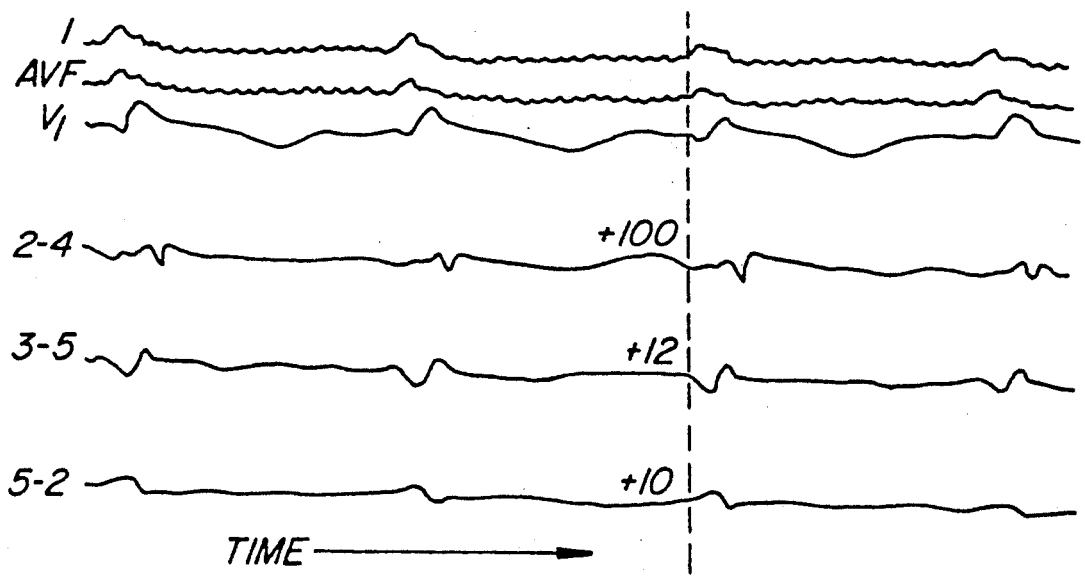
FIG._6A.
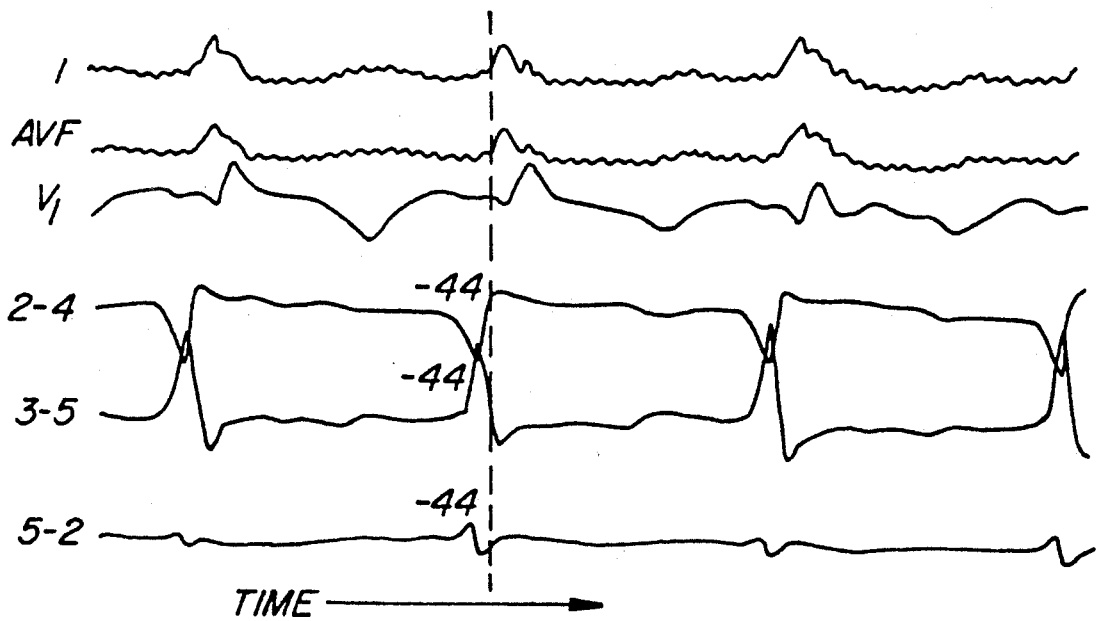
FIG._6B.

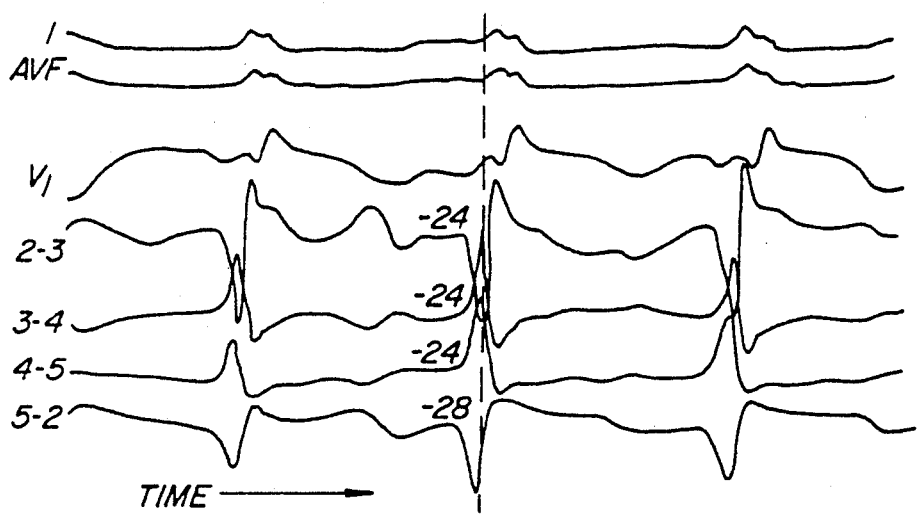
FIG._6C.
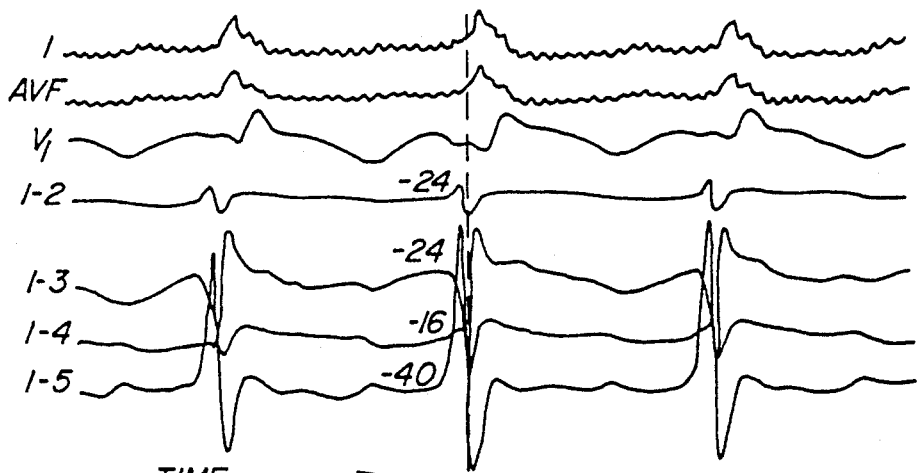
FIG._6D.
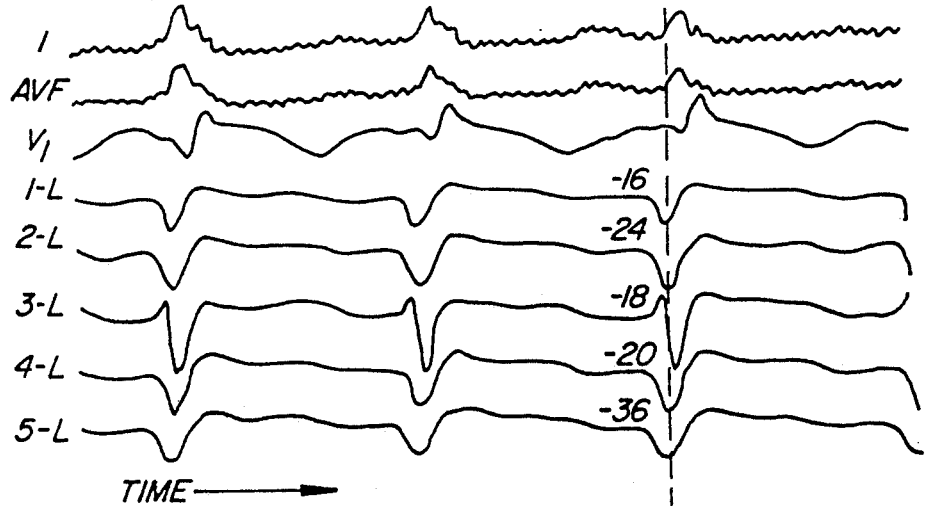
FIG._6E.

CATHETER FOR MAPPING AND ABLATION AND METHOD THEREFOR

This is a division of application Ser. No. 068,833, filed Jun. 10, 1987, now U.S. Pat. No. 4940064, which is a continuation-in-part of application Ser. No. 067931,696 filed Nov. 14, 1986 now abandoned.

BACKGROUND OF THE INVENTION

1. Field of the Invention

This invention relates to medical devices and in particular a multi-pole electrode catheter and method for endocardial mapping and ablation. A single catheter is capable both of mapping the atrial and ventricular heart chambers, as well as ablating foci or bypass tracts that cause dysrhythmias.

2. Description of the Prior Art

In the treatment of cardiac dysrhythmias, nonsurgical procedures such as management with drugs are favored. However, some dysrhythmias of the heart are not treatable with drugs. In addition, some patients of advanced age or illness may not tolerate invasive surgery to excise tachycardias which cause dysrhythmias.

Endocardial mapping is a technique that typically involves percutaneously introducing an electrode catheter into the patient. The electrode catheter is passed through a blood vessel, the aorta and and thence into an endocardial site such as the atrium or ventricle of the heart. A tachycardia is induced and a continuous, simultaneous recording made with a multichannel recorder while the electrode catheter is moved to different endocardial positions. When a tachardial foci is located as indicated in an electrocardiogram recording, it is marked by means of a fluoroscopic image.

Under earlier techniques, the mapping catheter would be withdrawn and replaced by an ablation catheter. The ablation catheter contained one or more electrodes for delivering a controlled burst of energy, of the order of 100 joules or so, to the foci. The foci would be ablated and the patient monitored for a period of time to ensure that there would be no reoccurence of the dysrhythmia. This removal of the mapping catheter was both time consuming as well as subject to inherent inaccuracies. This is because the location of the tachardial foci could not always be precisely relocated by using the fluoroscope.

As a result, catheters have been developed for the location and ablation of such tachycardias that perform both the mapping and ablation functions with the same catheter. One such mapping and ablation catheter is a hexipolar catheter made by the United States Catheter and Instrument Corporation. This prior art device has a series of six electrode rings in alternating 2 and 5 mm distances along an elongated woven Dacron surface. Bipolar electrograms are used to determine the site for ablation.

Problems with this and other prior art devices are manifest. First, the area of mapping is fairly large and imprecise. That is, the foci can only be found within about 10–12 cm$^2$ and at best only about 2–3 cm of the site.

Corollary to this is that the area ablated must be unduly large since the site of the foci is only known to this precision. The prior art electrode catheters also deliver the ablative charge over a wider than necessary area. This causes tissue and cell damage beyond the foci.

SUMMARY OF THE INVENTION

The invention is directed to an endocardial electrode catheter and method for performing both mapping and ablation functions in the same device. The catheter is in the form of a hollow tube having a plurality of side electrodes equally spaced around the distal end thereof. A further, central electrode is fixed to the distal end on the catheter axis. A like plurality of conductor wires pass through the hollow tube and are connected to leads which may be attached to a multichannel EKG machine for taking bipolar and unipolar electrograms. In an alternate embodiment, the wires pass through longitudinal bores within the tube wall.

A cable is contained within the tube and is fixed at its distal end to the central electrode. It is also connected to a lead which is, in turn, connected to the EKG machine. The cable passes through and is affixed to a hollow, elongated rod. The rod, in turn, passes through an end cap of a main body. An actuator knob on the proximal end of the rod allows the cable to be selectively retracted.

A plurality of slits intermediate the side electrodes allows the central electrode to be retracted vis-a-vis the side electrodes as the limbs intermediate and defined by the slits expand radially outwardly. The four side electrodes lie in the same plane and equally spaced from adjacent electrodes. The side electrodes are at the apexes of a square pattern with the central electrode in the center of the square.

A conduit leading to a chamber formed within the main body allows medicament to be conducted through the tube and out through the slits to the endocardial site of the distal end of the catheter.

To accomplish the method of mapping, the leads are connected to a multi-channel EKG machine. The distal end of the catheter is introduced into an endocardial site and recordings are made. The catheter is moved to different endocardial sites until a discontinuity shows on the EKG reading Before each move, the side electrodes are returned to their fully retracted mode. They are moved to their fully expanded mode when a new site is reached.

To accomplish ablation, the method further provides that electrical energy is then discharged through some or all of the leads and out of the respective electrodes. The electrical, radio frequency, or laser energy ablates the tachycardial foci which was found through mapping. If necessary, further ablation can be accomplished.

DESCRIPTION OF THE DRAWINGS

FIG. 1 is a front elevation view of a human heart in partial cross-section illustrating the distal end of the inventive catheter touching an endocardial surface, namely a ventricle wall;

FIG. 2 is a front elevation view of the catheter;

FIG. 3 is a partial cross-sectional elevational view of a portion of the catheter of FIG. 2, partially in cross-section to show details thereof;

FIG. 4A is an isometric view of the distal end of the catheter in the fully retracted mode;

FIG. 4B is a view of the same with the distal end of the catheter in the fully expanded mode;

FIG. 4C is a partial cross-sectional view taken along lines 4C–4C in FIG. 4A;

FIG. 5 is an enlarged partial cross-sectional view of an alternate embodiment of the catheter shown in FIG. 4A; and FIGS. 6A-6E are diagrams of EKG readings using the catheter.

DESCRIPTION OF THE PREFERRED EMBODIMENT

As shown in FIG. 1, the endocardial catheter of the instant invention is shown placed within a heart ventricle 12. As shown, the catheter is placed within the left ventricle, although it could as easily be placed within the right ventricle 14 or any other endocardial chambers or sites. For purposes of orientation the left ventricle is shown divided into four quadrants by dotted lines. These four quadrants are: right upper 2, right lower 4, left upper 6, and left lower 8.

Turning to FIG. 2, there is shown the inventive catheter 10 having a distal end 16 and a proximal end 18 at the opposite end thereof.

As shown in FIGS. 4A and 4B, the distal end 16 of the catheter is comprised of a generally hollow flexible tube portion 20 of a diameter small enough to be passed through the blood vessels and into the heart. As shown in these figures and in FIG. 3, tube 20 has an inner bore 22 of a lesser diameter than its outer diameter through which four electrically conductive wires shown generally at 24 pass. A centrally disposed cable 26 also shares the inner bore 22 of tube 20 with the plurality of wires 24 for a purpose to be hereinafter described. Tube 20 may be made of a flexible material such as plastic or Dacron. The distal end of tube 20 is fitted within a larger elongated tube 28. Tube 28 serves as a transition conduit between tube 20 and main body 30.

Main body 30 is made up of a series of components which form an interior chamber 32. Main body 30 consists of a necked-down hollow, generally frustoconical proximal end portion 34 and a generally cylindrical, hollow distal end portion 36 which are fitted within a cylindrical middle portion 38. Portions 34 and 36 are fitted within cylindrical middle portion 38 so as to leave a gap 40. This gap allows a side conduit 42 which is fixed to middle portion 38 at a perpendicular angle to the axis defined by the catheter to access the interior chamber 32 by way of an interior inlet bore 44. A flexible plastic conduit 46 is fitted over side conduit 42 for a purpose to be hereinafter described.

A cap 48 is threadedly fitted over the end 50 of distal end portion 36 by means of threads 51 so as to close off chamber 32. The various parts of main body 30 are conveniently made of plastic material.

Slidingly fitted within a centrally disposed hole 52 in end cap 48 is a tubular metal rod 54. Cable 26 is fitted within a proximal end 56 of rod 54. The distal end 58 of rod 54 has fixed thereon an actuator knob 60 through which exits the end 62 of cable 26. Insulation 64 around cable end 62 is provided where cable 62 exits activator knob 60. Insulation 66 is also provided where the plurality of wires 24 exit through a hole 68 in the side of proximal end portion 34. A plastic potting compound 70 seals the point of egress so that leakage out of chamber 32 is prevented. Similarly, a potting compound 72 is placed on the distal end of actuator knob 60 to seal insulation 64.

As shown in FIG. 2, the interior wires terminate in a plurality of electrode leads 74 (in this case, four). The cable terminates in a fifth electrode lead 76. A standard catheter fitting 78 on the end of conduit 46 permits connection with a medicament source (not shown). In this manner, medicament may be transferred through conduit 46 and into chamber 32, as best seen in FIG. 3.

As seen in FIG. 4A, the proximal end of catheter 16 is in its fully retracted position or mode. Because the catheter material has a "set" or "memory" it will normally return to this retracted position. In FIG. 4B, the proximal end of the catheter 16 is in its fully extended position or mode. Four electrodes 2, 3, 4 and 5 are mounted through and equally spaced around tube 20. These are of relatively small diameter compared with the centrally disposed electrode 1, which is fitted within the end 90 of distal end 16. The electrodes themselves may be made conveniently of a highly conductive material, such as gold or platinum. A plurality of longitudinally directed slits 92 are cut through 20 from a point adjacent to the end 90 thereof to a distance of approximately 1 millimeter away from said distal end. The slits define and form intermediate limbs 91 therebetween. The outer diameter of the tube itself may conveniently be about 2.34 millimeters.

In an example of operation, the catheter 10 is percutaneously introduced into a patient and directed through a blood vessel (not shown) and into the aorta 92, as best seen in FIG. 1. The distal end 16 is then positioned against an endocardial wall of, for example, the left ventricle 12.

At this point, actuator knob 60 is manually retracted to the position 60' as shown in FIG. 2. This causes the proximal end 16 of the catheter to be expanded so that the electrodes are at a first distance from each other equal to the tube outer diameter to its operative mode, as best shown in FIG. 4B. In this position, the plurality of side electrodes 2, 3, 4 and 5, are positioned equidistant from central electrode 1 and at a second distance which is greater than the first distance. The distance between adjacent side electrodes is conveniently about one centimeter. In this manner, an area of about one square centimeter of the endocardial wall is covered with central electrode 1 at the center of the square centimeter. As may be seen, side electrodes 2, 3, 4 and 5 are located on the upper half of the limbs formed by slits 92 so that the electrodes are presented in a proximal direction. Each side electrode is connected to a respective one of the electrically conductive wires, which are in turn connected to a respective one of the leads 74. The central electrode 1 is similarly connected through cable 24 to electrode lead 76.

Because the tip of the catheter is radio-opaque, it will be visualized by fluoroscopy. In this manner, it can be determined when the catheter tip is in contact with the endocardium. Alternatively, or at the same time, the electrocardiogram will indicate contact with the endocardium.

In an alternate embodiment shown in FIG. 5, the wires 24' pass through longitudinal bores 94 corresponding with each side electrode. In this manner, the wires are insulated from contact with each other and with cable 26'.

The method of operation of the inventive device will now be described as follows. The catheter is first used in mapping. Three surface electrocardiograms I, AVF and $V_1$, representing three planes (right to left, superior-inferior, anterior-posterior) are continuously monitored and the earliest deflection on any of these cardioelectrograms serves as a reference point (FIG. 6A). The catheter has five electrodes, the central electrode (number 1) and four electrodes, one on each limb (numbered clockwise 2, 3, 4, 5) as aforementioned. These five electrodes are attached to a multichannel recorder and the following combinations are recorded in bipolar and unipolar fashion. The bipolar electrode combinations are 2-4, 3-5, 5-2; 2-3, 3-4, 4-5, 5-2; 1-2, 1-3, 1-4, 1-5; and unipolar electrode combination are 1-L (limb), 2-L, 3-L, 4-L, 5-L (FIGS. 6A-6E).

The first electrode in any lead configuration serves as a positive electrode. The switching from one lead combination to another is accomplished by a solid state computerized selector box (not shown). The catheter is inserted through the leg artery (right femoral) and advanced to the aortic arch and then to the left ventrical utilizing fluoroscopic guidance. The ventricle or other heart chamber is arbitrarily divided into four quadrants, rights-superior and inferior, and left 1-superior and inferior quadrants.

The catheter is positioned in the right upper quadrant, limbs are deployed, tachycardia induced, and recordings obtained (FIG. 6A). Catheter limbs are retracted and the catheter moved to the lower quadrant (FIG. 68), in this way all four quadrants are mapped. The catheter is repositioned in the quadrant that demonstrates earliest intracardiac ECG with reference to earliest rapid detection on the surface ECG (FIG. 6B). Further manipulations of the catheter in that quadrant are undertaken so that intracardiac electrogram is very early as compared to the surface electrocardiogram and the unipolar intracardiac electrogram with one or more of its five electrodes documents earlier recording as compared with the surface electrocardiogram. These orthogonal and unipolar intracardiac electrograms from the catheter can assist in location of the site of origin of ventricular tachycardia by earliest intracardiac electrogram (with reference to surface electrocardiogram) and by amplitude and direction of intracardiac electrogram (FIGS. 6A-6E).

With specific reference to FIG. 6A, the ECG trace is shown with the catheter deployed in the right upper quadrant. A perpendicular dotted line is drawn from the earliest surface ECG, which in this case is lead I.

As may be seen, the intracardiac electrogram appears later in time than the surface ECG. As shown, the 2-4 trace is latest of the three traces (+100 milliseconds), 2-4, 3-5 and 5-2. The measurement point selected is the point of first rapid deflection. The time in milliseconds from the perpendicular to the first rapid deflection is indicated and juxtaposed with each trace.

FIG. 6B shows the ECG trace with the catheter moved to the right lower quadrant Again, a perpendicular dotted line is drawn from the earliest surface ECG which again proves to be lead I. In this example, all three traces of the intracardiac electrogram are early. All are almost equally early, which indicated that the catheter is close to the site of the ventricular tachycardia.

FIG. 6C shows the ECG trace in the same right lower quadrant as FIG. 6B above. However, the lead sequence has been changed as shown to record the earliest activity. The catheter has not been moved from its position from which the FIG. 6B traces were taken.

As shown, 5-2 lead trace is slightly earlier than the remaining 2-3, 3-4, and 4-5 traces. This indicates that the site is closer to lead 5-2 than to the others.

Turning to FIG. 60, the catheter still has not been moved. Rather, readings are taken between the center electrode 1, and each of the remaining peripheral electrodes. Since 1-5 is earliest, this indicates that the site is closest to electrode 5.

Finally, FIG. 6E is a unipolar (the previous graphs 6A through D were all bipolar) intracardiac ECG trace, again at the same location. Again, lead 5-L is the earliest, confirming that the site closest to electrode 5 is the earliest.

Further, construction of intracardiac vector loops form various coordinates of the catheter can facilitate finer catheter motion to precisely localize (within 1 sq. cm) the site of origin of ventricular tachycardia.

Once the earliest site is determined, ventricular tachycardia is terminated by standard methods (overdrive pacing or cardioversion). The catheter is held at the same site. A back plate providing a contact surface (not shown) is conveniently positioned beneath the patient to complete the circuit. The earliest site of origin is ablated by discharging energy (Electrical, Radiofrequency or Laser) through the catheter. For example, 25 to 100 Joules of energy can be delivered through one or more of the side electrodes. If only the central electrode is used, up to 300 Joules of energy can be used. The energy could be delivered through all five electrodes and back plate, central and back plate, four peripheral electrodes and central electrode or between two limb electrodes.

Alternatively, the back plate can be eliminated and current passed into one and out through one or more of the electrodes. An important feature of the instant invention is that the foci may be located with greater precision and the burning or ablation also directed with similar precision. Also, medicament may be passed through the open slits 92 and into the area of mapping and ablation.

After ablation has been completed, a time period is allowed to pass, such as for example ten minutes. The dysrhythmia is attempted to be reintroduced. If it is not introduced, the catheter is collapsed and removed from the patient. If dysrhythmia occurs, ablation is repeated, and so on. The patient is then watched or monitored for twenty-four to forty-eight hours to see if dysrhythmia occurs.

While the invention has been described in conjunction with a preferred embodiment thereof, it will be understood that the description is intended to illustrate and not limit the scope of the invention, which is to be defined by the scope of the appended claims.

I claim:

1. A multipolar electrode catheter having an elongated body defining a distal end and an opposite, proximal end, a plurality of electrodes mounted adjacent said distal end, said plurality of electrodes being spaced a first distance from each other, and expansion means for expanding the distance that said electrodes are spaced from each other a second, larger distance, wherein the number of said electrodes is four, and wherein said expansion means expands said electrodes into said second distance which is in the same plane, and wherein said electrodes are equally spaced from adjacent electrodes, and further including a fifth electrode centrally disposed intermediate said four electrodes, whereby said electrodes may be positioned against a site for mapping or ablation, and still further including retraction means for retracting from said second distance to said first distance.

2. The invention of claim 1 wherein said means for expanding the distance that said electrodes are expanded from each other is actuable from a position remote from said distal end, whereby said catheter may be operated from outside a patient while said distal end is positioned at an endocardial site.

3. A multipolar electrode catheter having an elongated body that is tubular in shape, defining an outer surface having a diameter and having an inner bore therethrough, said elongated body defining a distal end and an opposite, proximal end, a plurality of electrodes mounted adjacent said distal end on said outer surface, said plurality of electrodes being spaced a first distance from each other, and expansion means for expanding the distance that said electrodes are spaced from each other to a second, larger distance, said electrodes being in substantially the same plane at said second distance whereby all of said electrodes may be positioned against a substantially planar site for mapping or ablation at the same time when at said second distance.

4. The invention of claim 3 wherein said means for expanding the distance that said electrodes are expanded from each other is actuable from a position remote from said distal end, whereby said catheter may be operated from outside a patient while said distal end is positioned at an endocardial site.

5. The invention of claim 4 further including retraction means for retracting from said second distance to said first distance.

6. The invention of claim 3 wherein the number of said electrodes is four, and wherein said expansion means expands said electrodes into said second distance which is in the same plane, and wherein said electrodes are equally spaced from adjacent electrodes.

7. The invention of claim 6 further including a fifth electrode centrally disposed intermediate said four electrodes.

8. The invention of claim 3 wherein said catheter further includes a main body fixed to said distal end of said tubular member, said main body defining a chamber therein in fluid communication with said inner bore, and an inlet in said main body communicating with said chamber for admitting medicament for passage through said inner bore and out of said distal end.

9. The invention of claim 3 further including electrical conductor operatively connected to each of said electrodes for conducting electrical current thereto.

10. The invention of claim 9 further including a plurality of elongated bores formed in said elongated body, wherein the electrical conductors connected to said plurality of electrodes mounted adjacent to said distal end pass through said elongated bores.

11. A multipolar electrode catheter having an elongated body that is tubular in shape, defining an outer surface having a diameter and having an inner bore therethrough, said elongated body defining a distal end and an opposite, proximal end, a plurality of electrodes mounted adjacent said distal end on said outer surface, said plurality of electrodes being spaced a first distance from each other, and expansion means for expanding the distance that said electrodes are spaced from each other to a second, larger distance, whereby said electrodes may be positioned against a site for mapping or ablation wherein said expansion means comprises a plurality of slits in said tubular body each of said slits being located intermediate a pair of said electrodes and defining a plurality of limbs, and actuator means for moving said distal end toward said proximal end whereby said plurality of limbs move radially outwardly thereby moving said electrodes to said second distance from said first distance.

12. The invention of claim 11 wherein said catheter further includes a main body fixed to said distal end of said tubular member, said main body defining a chamber therein in fluid communication with said inner bore, and an inlet in said main body communicating with said chamber for admitting medicament for passage through said inner bore and out of said distal end.

13. The invention of claim 11 further including electrical conductor operatively connected to each of said electrodes for conducting electrical current thereto.

14. The invention of claim 13 further including a plurality of elongated bores formed in said elongated body, wherein the electrical conductors connected to said plurality of electrodes mounted adjacent to said distal end pass through said elongated bores.

15. A multipolar electrode catheter having an elongated body defining a distal end and an opposite, proximal end, a plurality of electrodes mounted adjacent said distal end, said plurality of electrodes being spaced a first distance from each other, and expansion means for expanding the distance that said electrodes are spaced from each other a second, larger distance, wherein the number of said electrodes is four, and wherein said expansion means expands said electrodes into said second distance which is in the same plane, and wherein said electrodes are equally spaced from adjacent electrodes, and further including a fifth electrode centrally disposed intermediate said four electrodes, whereby said electrodes may be positioned against a site for mapping or ablation, and wherein said means for expanding the distance that said electrodes are expanded from each other is actuable from a position remote from said distal end, whereby said catheter may be operated from outside a patient while said distal end is positioned at an endocardial site.

16. The invention of claim 15 further including retraction means for retracting from said second distance to said first distance.

17. A catheter having an elongated generally tubular body defining a diameter along its length and a central axis, said diameter being small enough in its tubular condition to pass through blood vessels and into the heart, said body defining a distal end and an opposite, proximal end, a plurality of electrodes mounted at least partially on the outside surface of said body and means for changing said distal end from said tubular condition to an expanded condition wherein said electrodes are moved radially outwardly to a substantially common plane, said plane being substantially perpendicular to said longitudinal axis.

18. The invention of claim 17 wherein one of said electrodes is a central electrode mounted on said distal end of said body substantially on said axis.

19. The invention of claim 17 wherein said means for changing also is also actuable to retract said distal end from its expanded condition to its initial, tubular condition.

20. The invention of claim 17 further including electrical conductors operatively connected to each of said electrodes for conducting electrical current thereto.

21. The invention of claim 20 further including a plurality of elongated bores in said body, and wherein said conductors connected to said plurality of electrodes pass through said elongated bores.

* * * * *